(12) United States Patent
Renesto et al.

(10) Patent No.: US 8,874,209 B2
(45) Date of Patent: Oct. 28, 2014

(54) DEVICE FOR CHARACTERIZING THE CARDIAC STATUS OF A PATIENT EQUIPPED WITH A BIVENTRICULAR PACING ACTIVE IMPLANT

(75) Inventors: Fabrizio Renesto, Borgofranco (IT); Filippo Ziglio, Martignano (IT)

(73) Assignee: Sorin CRM S.A.S., Clamart Cedex (FR)

( * ) Notice: Subject to any disclaimer, the term of this patent is extended or adjusted under 35 U.S.C. 154(b) by 1485 days.

(21) Appl. No.: 12/331,286

(22) Filed: Dec. 9, 2008

(65) Prior Publication Data
US 2009/0157134 A1 Jun. 18, 2009

(30) Foreign Application Priority Data
Dec. 13, 2007 (FR) .................................... 07 08681

(51) Int. Cl.
*A61N 1/00* (2006.01)
*A61N 1/362* (2006.01)
*A61N 1/365* (2006.01)
*A61N 1/368* (2006.01)

(52) U.S. Cl.
CPC ........... *A61N 1/3627* (2013.01); *A61N 1/36578* (2013.01); *A61N 1/3682* (2013.01); *A61N 1/3684* (2013.01); *A61N 1/36542* (2013.01)
USPC .............................................................. 607/9

(58) Field of Classification Search
None
See application file for complete search history.

(56) References Cited

U.S. PATENT DOCUMENTS

| | | | |
|---|---|---|---|
| 5,304,208 A | 4/1994 | Inguaggiato et al. | |
| 5,496,351 A | 3/1996 | Plicchi et al. | |
| 5,693,075 A | 12/1997 | Plicchi et al. | |
| 6,556,866 B2 | 4/2003 | Dal Molin et al. | |
| 7,409,241 B2 | 8/2008 | Vitali et al. | |
| 7,664,547 B2 | 2/2010 | Plicchi et al. | |
| 7,792,574 B2 | 9/2010 | Casset | |
| 2005/0027320 A1 | 2/2005 | Nehls et al. | |
| 2007/0179542 A1 | 8/2007 | Prakash et al. | |

FOREIGN PATENT DOCUMENTS

| | | |
|---|---|---|
| EP | 0515319 | 11/1992 |
| EP | 0655260 | 5/1995 |
| EP | 1108446 | 6/2001 |
| EP | 1533001 | 5/2005 |
| EP | 1736203 | 12/2006 |
| EP | 1867360 | 12/2007 |

OTHER PUBLICATIONS

Foreign Search Report (Annexe Au Rapport De Recherche Preliminaire; Ralatif A La Demande De Brevet Francais No. FR 0708681 FA 701023), Jun. 16, 2008.
Daubert, J. C. et al., *Stimucoeur*, vol. 25, No. 3, 1997, pp. 170-176.
European Search Report dated Apr. 7, 2009 as received in corresponding European Patent Application No. 08291086.0.

*Primary Examiner* — Christopher D Koharski
*Assistant Examiner* — Elizabeth K So
(74) *Attorney, Agent, or Firm* — Foley & Lardner LLP

(57) ABSTRACT

A medical device for characterizing the cardiac status of a patient equipped with a bi-ventricular pacing active implant device. The implant collects an endocardiac acceleration signal and searches for an optimal pacing configuration. This latter tests a plurality of different pacing configurations and delivers for each tested configuration parameters derived from the endocardiac acceleration peak (PEA). The device derives a patient clinical status from those parameters, the indication being representative of the patient's response to the cardiac resynchronization therapy. Those parameters include: the possibility to automatically get or not a valid optimal AV Delay among all the biventricular pacing configurations; a factor indicating the character sigmoid of the PEA/ AVD characteristic; the average value of the PEA for the various configurations; and the PEA signal/noise ratio. The active implantable medical device includes control software and processes for executing the characterizing functionality described.

12 Claims, 6 Drawing Sheets

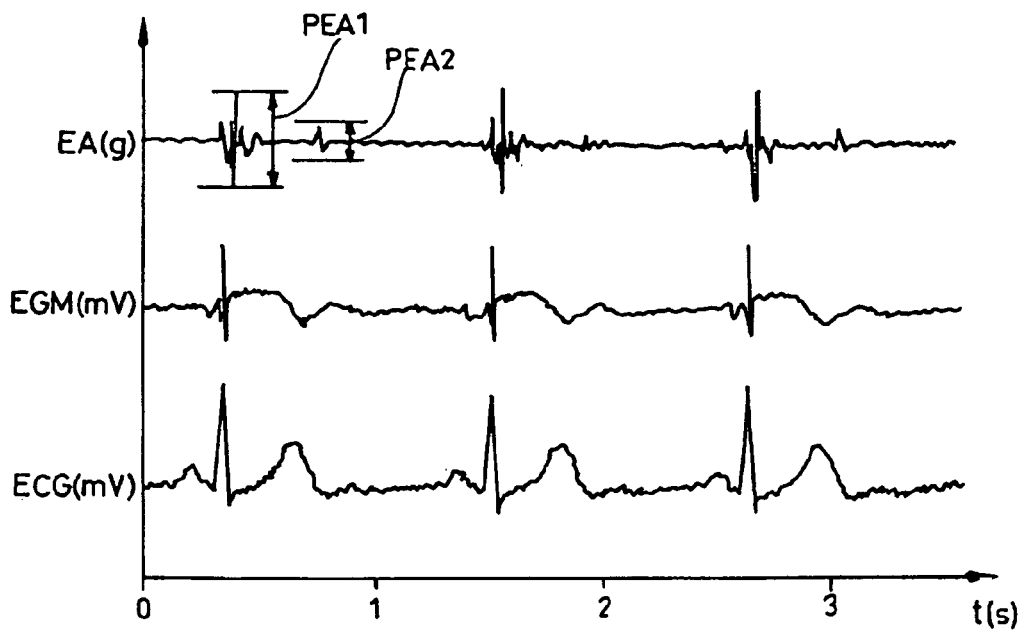
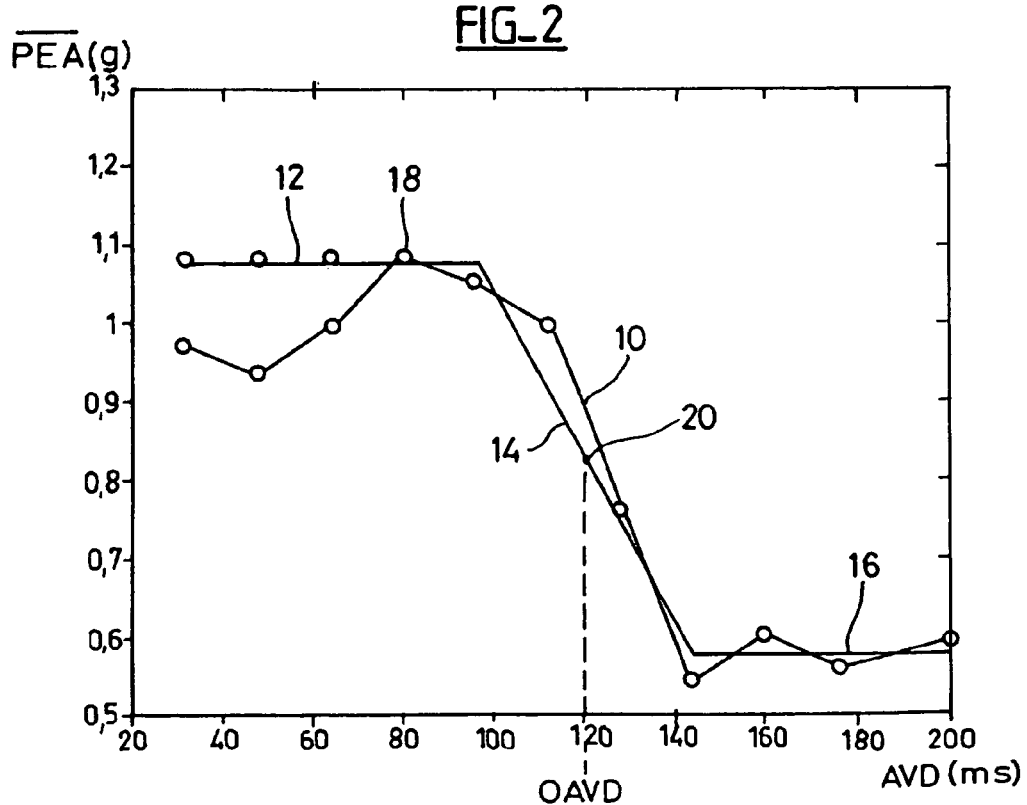

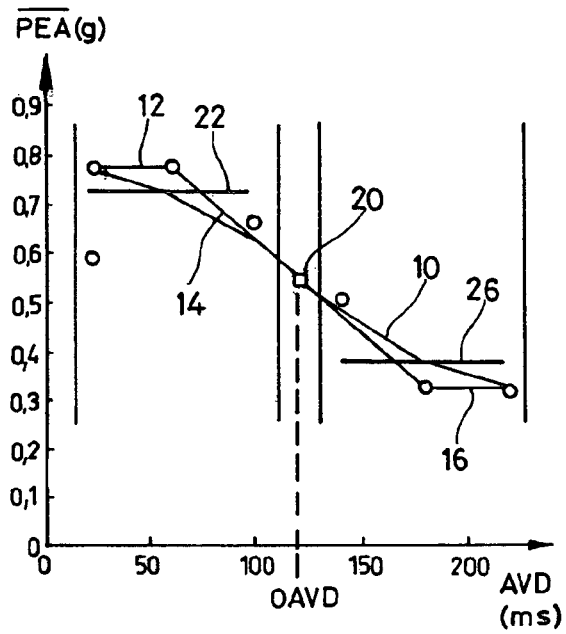
FIG_3a
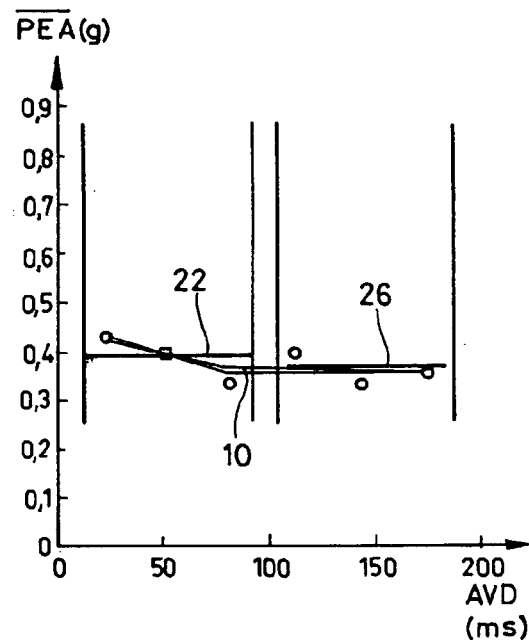
FIG_3b
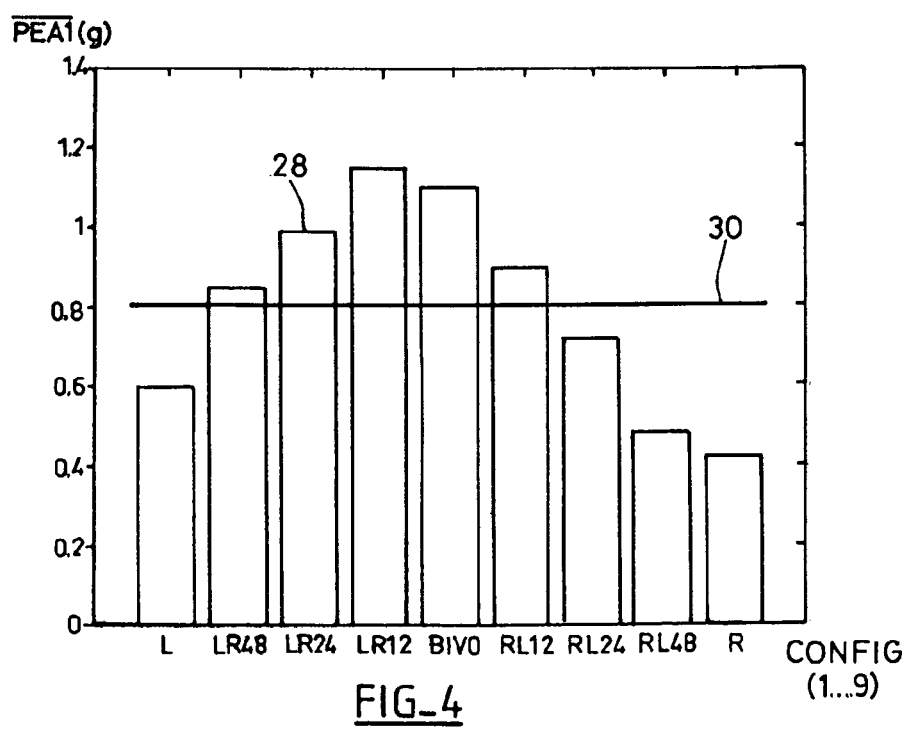
FIG_4

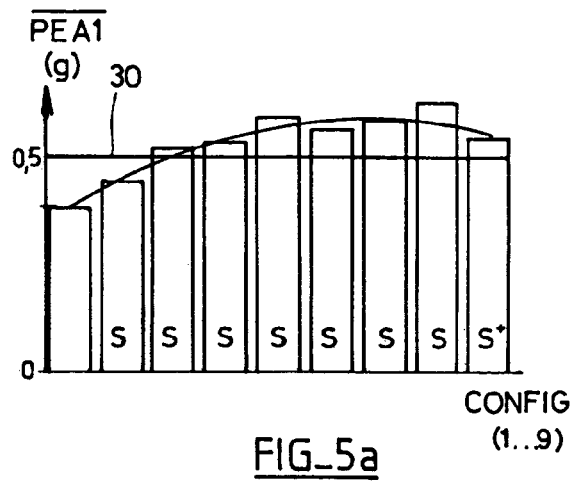
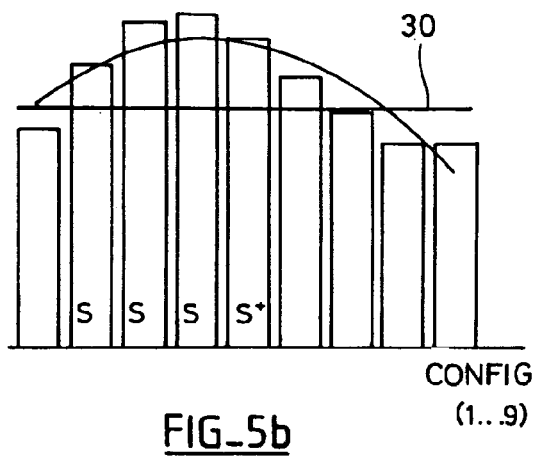
FIG_5a
FIG_5b
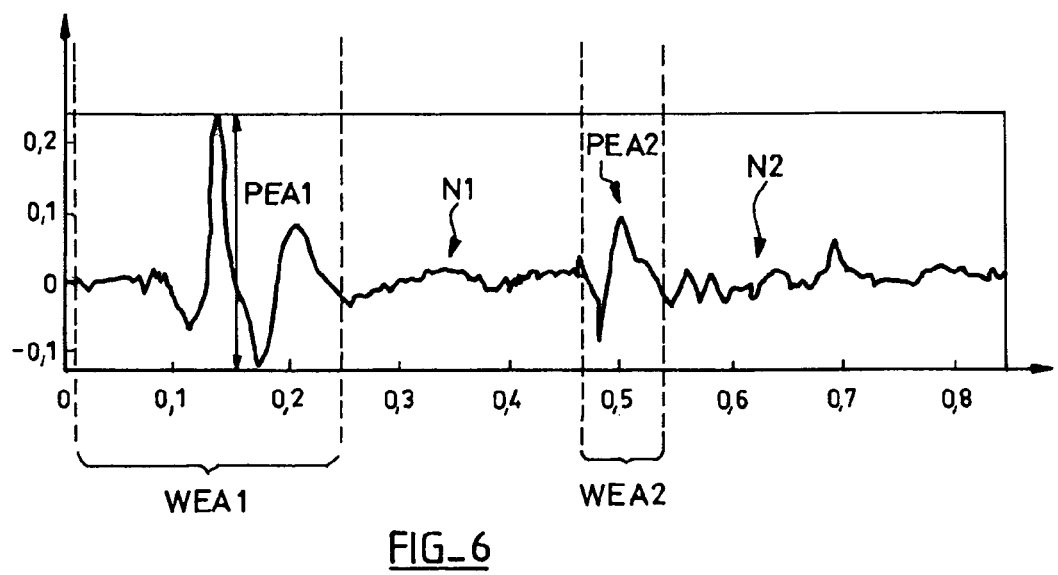
FIG_6

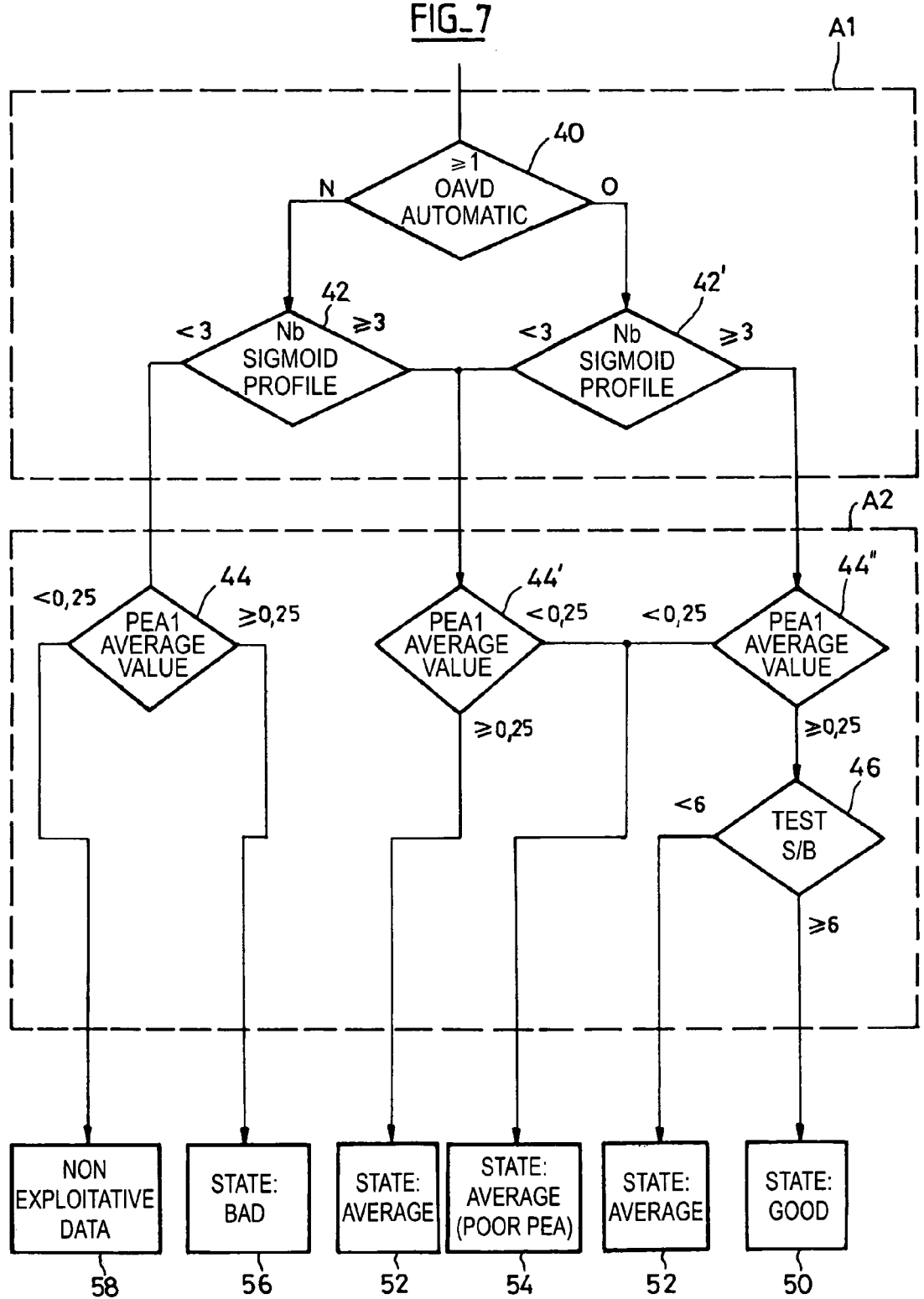

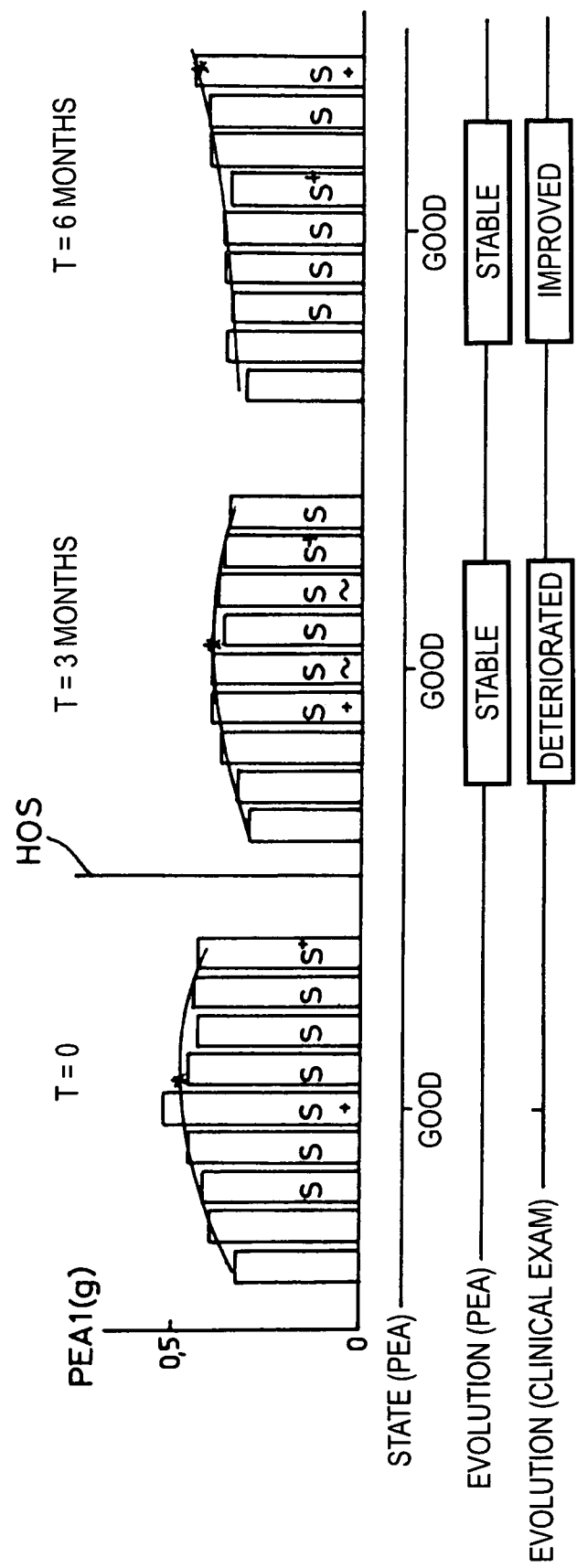

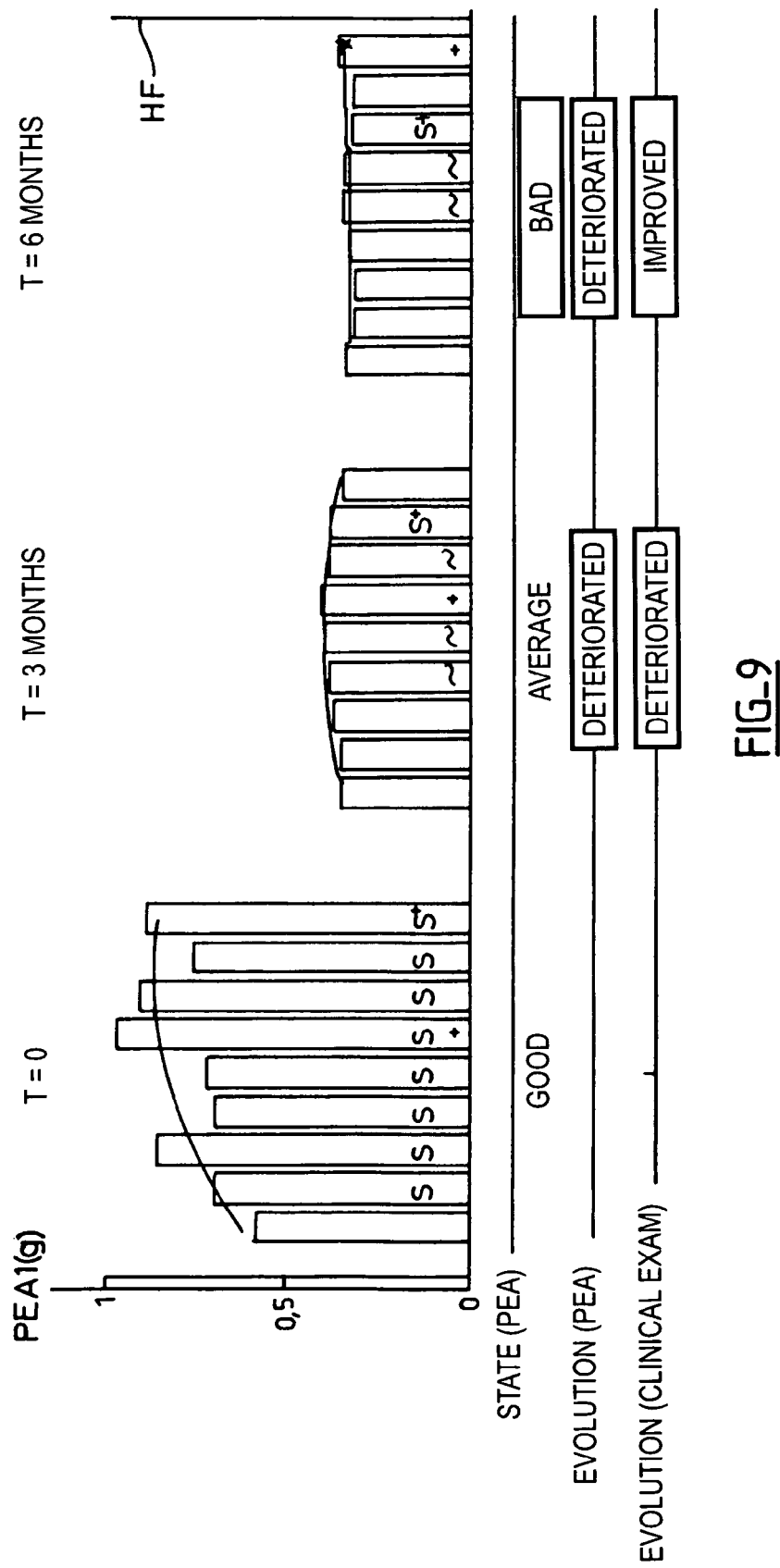

DEVICE FOR CHARACTERIZING THE CARDIAC STATUS OF A PATIENT EQUIPPED WITH A BIVENTRICULAR PACING ACTIVE IMPLANT

FIELD OF THE INVENTION

The present invention relates to "active implantable medical devices" as such devices are defined by the Jun. 20, 1990 Directive 90/385/CEE of the Counsel of the European Community, and more particularly to implants that allow continuous monitoring of the cardiac rhythm and deliver to the heart, if necessary, the electrical pulses required to ensure a joint and permanent pacing of the right and left ventricles in order to resynchronize them, which technique is known as "CRT" (Cardiac Resynchronization Therapy) or "BVP" (Bi-Ventricular Pacing).

BACKGROUND OF THE INVENTION

As an alternative or in addition to the treatment of the cardiac rhythm disorders, a biventricular pacing has been proposed for some myocardium contraction disorders observed in patients suffering from heart failure, which disorders are spontaneous or induced by a traditional pacing technique. One can refer, for example, to a study from J. C. Daubert et coll., Stimucoeur, 25, #3, pp. 170-176 which gives a global overview of the topic. This therapy often induced spectacular results for patients suffering from class III heart failure and not improved by traditional treatments.

A CRT pacemaker is, for example, disclosed in the EP 1 108 446 A1 (and its counterpart U.S. Pat. No. 6,556,866 B2) (ELA Medical), which describes a device able to establish a variable interventricular delay between the two ventricles, tuned so as to resynchronize the ventricle contractions with fine optimization of the patient Haemodynamic.

Many currently used CRT devices are "multi-site" prostheses in which coils are implanted in a plurality of distinct sites, including at least one atrial site in addition to the right and left ventricle sites, as in the so-called "triple chamber" (dual ventricular pacing and sensing/pacing of the right atrium) or "quadruple chamber" (dual ventricular pacing and dual sensing/pacing of the atriums) devices. There are also multi-site devices where one of the ventricle leads is implanted in the right ventricular apex and the other in a position chosen to optimize the ventricular resynchronization.

One can define "pacing sites" as the physical location where the intra-cardiac electrodes are in the myocardium. Those sites can be chosen during the implant procedure by an appropriate positioning of the electrodes. When the device comprises several electrodes in a same cardiac cavity, a modification of the pacing site is then possible by an internal switching inside the device.

The notion of "pacing sequence" is related, on one hand, to the order in which the pacing pulses are delivered to the heart (for example: atrium first, then left ventricle, then right ventricle) and, on the other hand, to the timings between the application of these various successive pulses. The pacing sequence is defined at implant and can be, if necessary, subsequently changed by appropriate internal switches of the device and by adjustments of the pacing sequence parameters.

One can define the "pacing configuration" as the combination of the characteristics related to the "pacing sites" and of those related to the "pacing sequence".

It is necessary to evaluate the relevancy of the selected pacing configuration, for this impacts the efficiency of the bi-ventricular pacing therapy. Furthermore, the positive effects procured by this therapy can lead, in the long term, to re-evaluate the initial configuration to eventually change the sites and/or the pacing sequence parameters.

The ultrasound-based evaluation techniques that shall be implemented in the hospital environment by a qualified personnel are expensive and can not be used as often as necessary without interfering with the daily life of the patient.

A solution described in the aforementioned patent EP 1 108 446 A1 concerns in evaluating the degree of synchronization of the right and left ventricle contractions by an intra-cardiac bio-impedance measurement. This data are indeed representative of the cardiac flow and, therefore, of the ejection fraction, considered as being the reference Haemodynamic parameter.

The present invention is based on another approach of the optimization of the bi-ventricular pacing, implementing an analysis of the endocardiac acceleration, and more precisely an analysis of the endocardiac acceleration peaks.

Indeed, clinical studies have indicated that the endocardiac acceleration is a parameter that provides very comprehensive information of the myocardium functional state, in the case of a normal functioning as well as in a deficient one: the endocardiac acceleration, which is measure by an accelerometer directly in contact with the cardiac muscle (generally, but not exclusively, at the right ventricle apex, sometimes in the right atrium) very precisely reflects, in real time, the converging phenomenon of the mechanical functioning of the heart.

More precisely, the EP 0 515 319 A1 (and its counterpart U.S. Pat. No. 5,304,208) (Sorin Biomedica Cardio SpA) teaches a useful manner to collect the endocardiac acceleration signal by means of an endocardiac lead equipped with a distal pacing electrode implanted in the ventricle and integrating a micro-accelerometer allowing to measure the endocardiac acceleration. The endocardiac acceleration signal collected during a cardiac cycle presents two peaks, corresponding to the two major sounds that it is possible to identify in each cycle of a healthy heart:

the first endocardiac acceleration peak ("PEA1") corresponds to the closing of the mitral and tricuspid valves, at the beginning of the iso-volumetric ventricular contraction (systole). The variations of this first peak are narrowly linked to the pressure variations in the ventricule (the amplitude of the PEA1 peak being, more precisely, correlated to the positive maximum value of the pressure variation dP/dt in the left ventricle) and can therefore constitute a representative parameter of the myocardium contractility, which is linked to the activity level of the sympathetic system;

the second endocardiac acceleration peak ("PEA2") corresponds to the closing of the aortic and pulmonary valves, at the moment when the iso-volumetric ventricular relaxation occurs. This second peak, induced by the rapid deceleration of the blood mass moving in the aorta is a representative parameter of the protodiastolic blood pressure in the beginning of the diastole.

The EP 0 655 260 A1 (and its counterparts U.S. Pat. No. 5,693,075 and U.S. Pat. No. 5,496,351) (Sorin Biomedica Cardio SpA) describes a useful manner to process the endocardiac acceleration signal delivered by the sensor located in the end of the lead to deliver two values linked to those respective endocardiac acceleration peaks. These values are notably useful for the detection of cardiac rhythm disorders and whether or not to trigger a defibrillation therapy.

The EP 1 736 203 A1 (and its counterpart FR 2 887 460 A1 and U.S. patent application Ser. No. 11/425,668 filed Jun. 21, 2006) (ELA Medical) describes an application specific to bi-ventricular implantable pacemakers, using the parameters linked to the endocardiac acceleration to determine an optimal pacing configuration for the patient, during implant or after. Various measurements are performed to characterize the PEA signal and are combined to give a composite performance indication, the final pacing configuration chosen being the one that maximizes this performance indication.

OBJECTS AND SUMMARY OF THE INVENTION

The starting point of the present invention is the recognition by the inventor that one can use the endocardiac acceleration data collected by the known device and processed by the implant for an additional purpose, namely to evaluate at any given moment, the clinical status of the patient, that is to say the response of the patient to the cardiac resynchronization therapy. An indication of the clinical status will allow following the patient's ventricular function in the long term, preferably to evaluate the risks that a heart failure episode occurs.

In other words, the present invention proposes to use certain data already calculated by the implant in connection with optimizing the pacing configuration (preferably in the manner described in the already cited EP 1 736 203 A1 (and corresponding FR 2 887 460 A1 and U.S. patent application Ser. No. 11/425,668 filed Jun. 21, 2006). This data are then processed, in a manner described hereafter to produce an indication of the clinical status of the patient.

In one embodiment, the invention can be implemented by the use of an external device such as a programmer of the kind used by physicians during routine patient follow-up visits to interrogate and optionally change the parameters of the implant. But other solutions can be implemented. For example, in a preferred embodiment, inside the implant, the clinical data can be processed and used to trigger an alarm designed to warn the patient and/or to be transmitted to a distant call center in charge of ensuring the patient's follow-up based on the remotely transmitted data collected.

In a particular implementation, the present invention uses one of the techniques described in EP 1 736 203 A1 (FR 2 887 460 A1; U.S. Ser. No. 11/425,668), that obtains for each pacing configuration a PEA/AVD characteristic by executing a sweeping of the AV Delay (AVD) while recording the variations of the Peak Endocardiac Acceleration (PEA), generally the first peak, PEA1. This characteristic can be obtained by periodic activation, for example, in a test mode triggered by the implant. The collected results are, according to the invention, used during the test to determine an indication of the clinical status of the patient, in addition to the verification of the selected pacing configuration.

Thus, broadly, the present invention is directed to a medical device that can characterize a cardiac status of a patient equipped with an active implant that delivers a cardiac resynchronization therapy by bi-ventricular pacing. The implant collects an endocardiac acceleration signal and searches for an optimal pacing configuration. This latter tests a plurality of different pacing configurations and delivers for each tested configuration parameters derived from the endocardiac acceleration peak (PEA). The device derives a patient clinical status from those parameters, the indication being representative of the patient's response to the cardiac resynchronization therapy. Those parameters include: the possibility to automatically get or not a valid optimal AV Delay among all the biventricular pacing configurations; a factor indicating the character sigmoid of the PEA/AVD characteristic; the average value of the PEA for the various configurations; and the PEA signal/noise ratio. Control software for executing the functionality and method steps are provided for an active implantable medical device and/or a remote programmer.

One such device is an implant of the general type disclosed in aforementioned EP 1736203 A1 (FR 2887460 A1; U.S. Ser. No. 11/425,668) that is able to deliver biventricular cardiac resynchronization therapy, including:

means for bi-ventricular pacing at selected ones of a plurality of pacing sites;

means for collecting an endocardiac acceleration signal (EA);

means for testing a plurality of different pacing configurations by changing at least one of (i) the selected sites, (ii) a pacing pulse sequence applied to the selected sites and (iii) a time interval between the application of the pacing pulses to the selected sites;

means for searching for an optimal pacing configuration using said testing means for each tested pacing configuration, delivering a plurality of parameters derived from one of the two endocardiac acceleration peaks (PEA1, PEA2) that appear respectively during the iso-volumetric and during the iso-volumetric ventricular relaxation; and means for characterizing a patient cardiac status comprising:

means for analyzing said plurality of parameters to derive a corresponding plurality of different respective specific indications, and means for combining said specific indications in a composite indication of the patient clinical status representative of the patient response to the cardiac resynchronization therapy.

In one embodiment, the device includes a sweeping means for varying an AV Delay (AVD) between an atrial sensed or paced event and a consecutive ventricular pacing event, and the characterizing means analyzes a PEA/AVD characteristic, giving successive endocardiac acceleration PEA peaks as a function of the AV Delay. More preferably, the characterizing means determines an optimal AV Delay (OAVD) by analysis of the PEA/AVD characteristic for a plurality of different biventricular pacing configurations, and the composite clinical status indication depends on whether or not a valid optimal AV Delay has been reached, among all of the different biventricular pacing configurations.

Further, the characterizing means may include means for modeling said PEA/AVD characteristic in three segments, having two plateaus from one side and a central segment with a negative slope, and wherein said composite clinical status indication is a function of the relative position of those three segments.

In an alternate embodiment, the characterizing means operates to determine a representative factor of a sigmoid character of the PEA/AVD characteristic for a plurality of different biventricular pacing configurations, and the clinical status composite indication is a function of the determined sigmoid factor. More preferably, the composite clinical status indication is also a function of the number of configurations, among all the different biventricular pacing configurations, for which the corresponding sigmoid factor is above a predetermined threshold.

In yet another embodiment, the characterizing means includes means for calculating an amplitude average value of the detected endocardiac acceleration peaks for a plurality of different pacing configurations, wherein the clinical status composite indication is a function of the average value.

Yet another embodiment provides the characterizing means as including means for quantifying the signal/noise ratio of the detected endocardiac acceleration peak, wherein the composite clinical status indication is a function of the result of the signal to noise quantification.

Preferably, the characterizing means includes means for comparing each of the specific indications to predetermined respective criteria, and a Boolean table that provides a corresponding value of the composite indication in response to the comparison. The comparison may be comparing first level (A1) specific indications derived from a PEA/AVD characteristic and including:
    A first specific indication indicating whether at least one optimal AV Delay has been reached or not, and
    A second specific indication representative of the sigmoid factor of said PEA/AVD characteristic.
The comparison also may include comparing a second level (A2) specific indications including:
    A third specific indication derivate from an average value of the endocardiac acceleration peaks, and
    A fourth specific indication derivate from a quantification of the endocardiac acceleration peak signal/noise ratio.
In addition, the characterizing means preferably includes:
    means for analyzing an evolution versus time of at least two successive values of said composite clinical status indication, and
    means for deriving from said analysis an indication of the patient evolution indicator and of the risk that a heart failure episode occurs.

BRIEF DESCRIPTION OF THE DRAWINGS

Further features, advantages and characteristics of the present invention will be apparent to a person of ordinary skill in the art based on the following detailed description of a preferred embodiment of the invention, made with reference to the attached drawings, in which the same numerical references designate from one drawing to another identical or functionally similar elements, and in which:

FIG. 1 is a chronogram showing, during three consecutive cardiac cycles the variations of the endocardiac acceleration, as well as those of the electrogram and those of the surface electrocardiogram;

FIG. 2 shows a PEA/AVD characteristic giving the variation of the endocardiac acceleration peak as a function of the AV Delay, and explains how to model this characteristic in three consecutive segments;

FIGS. 3a and 3b respectively show a PEA/AVD characteristic with a satisfactory convergence and a not sufficient convergence;

FIG. 4 shows the various levels of the endocardiac acceleration peak when successively testing all the possible pacing configurations in a same patient and the average value of the same parameter;

FIGS. 5a and 5b are homologous to FIG. 4, to illustrate the collected parameters at a three month interval in a same patient;

FIG. 6 shows a manner to determine the signal/noise ratio of the endocardiac acceleration peak value;

FIG. 7 is a flow-chart showing a manner by which the indication of the clinical status of the patient is determined from the different parameters measured by the implant; and FIGS. 8 and 9 show, for two clinical cases given as an example, the evolution with time of a calculated indication of the invention, compared to a clinical evolution determined by traditional means by a physician.

DETAILED DESCRIPTION OF THE INVENTION

With reference to the drawings, a preferred embodiment of a device in accordance with the present invention will be described. With reference to FIG. 1, the upper curve illustrates the variations of the endocardiac acceleration (EA) measured by a sensor similar to the one described in EP 0 515 319 A1 and U.S. Pat. No. 5,304,208, integrated in an endocardiac lead implanted in the bottom of the ventricle. Also displayed are Electrogram (EGM) curves, that is: the electrical signal collected through the distal electrode of the same sensor, and a corresponding surface electrocardiogram (ECG), during three consecutive cardiac cycles. As explained above, the curve of the acceleration shows two complexes or successive endocardiac acceleration peaks (PEA), the amplitude and the duration of which can be determined by an appropriate signal delivered by the acceleration sensor processing. This is described in EP 0 655 260 A1 (by "peak amplitude", one means the maximum and minimum values of the acceleration signal separating two positive and negative extremes, corresponding to the PEA1 and PEA2 indicated on the chronogram of FIG. 1; by "peak duration", one means the timing interval between the beginning and the end of the complex).

The already cited EP 1 736 203 A1 and U.S. Ser. No. 11/425,668, to which one can refer for additional details, which is incorporated by reference herein in its entirety, describes a manner to use certain parameters linked to the endocardiac acceleration and collected to automatically determine an optimal pacing configuration for the patient, at the time of implant as well as later on. Various parameters can be used for this, notably: the PEA1 amplitude and/or the PEA2 amplitude, the PEA1 duration and/or the PEA2 duration, the timing between the PEA1 and the consecutive associated PEA2, the timing interval between the PEA2, and the consecutive PEA1 of the next cycle.

In the following description, when referring to "PEA", one will essentially mean the parameters linked to the first peak (PEA1), which is generally, the most significant. But this characteristic is not limitative, and it should be understood that the invention can also be implemented based on data relative to the second peak (PEA2), or based on a combination of data from PEA1 and PEA2.

As described in EP 1 736 203 A1, during a specific phase the purpose of which is to evaluate and optimize the pacing configuration, the implant tests the possible pacing configurations and preferably measures the amplitudes of the PEA in each of these configurations. Another function implemented in this test algorithm and process concerns, for a given configuration, making the AV Delay vary and collecting the corresponding PEA amplitude values. The algorithm then allows adjusting the AVD on an optimal value of the AV Delay (OAVD), once a particular pacing configuration is selected.

The results collected during these tests are, according to the present invention, used to determine an indication of the clinical status of the patient. In the following example, this indication is determined from among the four following parameters:
    convergence of the AVD search algorithm (optionally to determine an optimal AVD),
    sigmoid character of the PEA/AVD characteristic;
    average value of the PEA amplitudes in the various possible pacing configurations, and
    (optionally) quantification of the PEA signal/noise ratio.

Convergence of the AVD Research Algorithm

A PEA/AVD characteristic, similar to characteristic 10 on FIG. 2, can be obtained by making the AVD vary and collecting the PEA amplitudes (generally the PEA 1). The PEA amplitude has a sigmoid appearance when the AVD varies between two extremes, typically between 30 and 200 ms. One can interpret this curve considering that the decreasing amplitude of the PEA as the AV delays increase is determined by two main factors, which are:

"the contractility reserve" of the myocardium, corresponding to the level of the baseline (limit value of the PEA for long AV Delays), and "the noise" produced by the cardiac valves, mainly the mitral valve, which determine the elevation of the amplitude level above this baseline, for the shortest AV Delays.

In order for the second component to be significantly present, it is necessary that the first one is present, because the myocardium contractility is the "driving force" for the entire mechanical phenomenon that occurs during the cardiac cycle.

This PEA/AVD characteristic collected during the test phase is analyzed by an algorithm designed to determine an optimal value of the AVD, hereafter described as OAVD. Clinical studies have demonstrated that the ability of this algorithm to calculate such an OAVD value (convergence of the algorithm) is a major indication of good ventricular condition of the patient. Essentially, it is possible to get an OAVD (i.e., to make the algorithm converge) if the PEA/AVD characteristic shows a tidy sigmoid appearance, with a significant slope between the short and long values of AVD. Clinical studies in particular have demonstrated a good correlation between the middle point of this curve and the optimal AV Delay provided by traditional echocardiography techniques.

We will now describe an example of algorithm and process that may be implemented in control software allowing one to obtain an optimal OAVD value of the AV Delay. The characteristic 10 provided when collecting the PEA amplitude signals is modelled by means of three successive continuous segments, with a horizontal plateau 12 corresponding to small AV Delays, a central inclined segment 14 corresponding to intermediate AV Delays and an horizontal plateau 16 corresponding to large AV Delays.

The algorithm researches, among the lower values of AVD, the one that provides the maximum value of PEA; this value is referenced 18 on the example illustrated in FIG. 2. All the PEA values collected for an AVD below this maximum value are then replaced by this maximum value, which defines the level of the upper plateau 12.

The two other segments 14 and 16 are then determined by linear regression, in a manner which is already known, so as to determine the narrowest adjustment between the three segments 12, 14 and 16 and the real characteristic 10. The adjustment between the three segment curve and the characteristic 10 is evaluated by mean of a convergence indication (IC), based on the linear regression, which minimises the sum of the square tests:

$$IC = 1 - \frac{\chi^2}{\chi^2_{ref}}$$

with:

$$\chi^2 = \chi^2_{upper} + \chi^2_{lower} + \chi^2_{slope}$$

and:

$$\chi^2_k = \sum_i (Pea_i - k)^2$$

$$\chi^2_{ref} = \sum_N (Pea_N - \overline{Pea})^2$$

The best adjustment is the one considered being the one that provides the maximum value of the IC convergence indication. The optimal OAVD of the AV Delay is considered as the one located in the middle 20 of the slopping central segment 14.

The algorithm validates this optimal OAVD, by verifying a certain number of criteria. It considers that an optimal AV Delay OAVD is "valid" if the three following conditions are cumulatively fulfilled:

IC convergence indication greater than or equal to a given threshold, for example 0.76 (value that reflects a good adjustment of the modeled curved to the real characteristic);

OAVD delay value greater than a given minima threshold, for example, OAVD greater than or equal to 55 ms;

Difference of levels, between upper plateau 12 and lower plateau 16, greater than or equal to 0.15 g (or 10% of the average value of the PEA amplitude of the characteristic)

The above values are, of course, only given as representative examples; they result from clinical studies performed to validate the invention, but do not have any limitative characteristic and other values could be employed within the spirit and scope of the present invention.

Sigmoid Nature of the PEA/AVD Characteristic

This parameter allows discriminating, among the several characteristics collected, those which have a really significant sigmoid nature, which is a central segment with a significant slope, compared to "flatter" curves from which one can not collect significant indications. To make this distinction, a parameter known as "sigmoid factor" or "SF" is calculated, from average values of the PEA amplitude from left and right sides of the characteristic (it should be understood that the term "sigmoid" in its most comprehensive meaning, including, in particular, the situations where the characteristic is assimilated, like it sometimes happens, to be a simple straight line with a negative slope. These indications are graphically illustrated on FIGS. 3a and 3b, respectively for a characteristic that shows a significant sigmoid characteristics, and for a much flatter characteristic.

Indeed, in the case of a bi-ventricular pacing, an efficient pacing configuration is synonymous with an accentuated PEA/AVD characteristic for short AV Delays, as illustrated on FIG. 3a. On the contrary, in case of heart failure, when the myocardium contractility reserve is minimal, the reduction of the ventricular filling for the shortest AV Delays provokes a contractility decrease resulting from the Frank-Starling's law. For short AV Delays, a much lower increase of the PEA amplitude induced by the cardiac valve "noises" is obtained than on healthy patients, as shown on FIG. 3b, this increase being sometimes hardly visible.

The determination of the sigmoid factor SF is made by comparing the average levels referenced respectively as 22 and 26 on those figures. The calculation is made by the following formula:

$$SF = 1 + \frac{\sum_{i=2}^{3} Pea_i - \sum_{i=5}^{6} Pea_i}{\sum_{i=2}^{3} Pea_i + \sum_{i=5}^{6} Pea_i}$$

A SF value lower than 1 corresponds to a reversed curve, a SF value of around 1 corresponds to a flat curve, and a SF value higher than 1 corresponds to a searched sigmoid, decreasing curve. The higher the SF is, the stronger the sigmoid characteristic is (in this way, the two examples illustrated in FIGS. 3a and 3b correspond to sigmoid values of respectively SF=1.3831 and SF=1.0176). A statistical evaluation performed during clinical studies shows that a threshold superior or equal to 1.12 corresponds to a significant value, with a sensitivity of 79% and a specificity of 81%.

The algorithm performs this analysis of the sigmoid characteristic of the PEA/AVD characteristic for all the possible pacing configurations and determines, for each of them, if the SF factor is above the predetermined threshold or not. The higher the number of characteristics is, the higher the probability to optimize the pacing is (selection of the configuration and AVD adjustment), with, as a consequence, higher chances that the patient satisfactory responds to the cardiac resynchronization therapy.

Average Values of the PEA Amplitudes

Another parameter taken into account by the algorithm is the average value of the PEA for all the possible pacing configurations. FIG. 4 illustrates a result of this measurement for nine possible configurations, designated as L (left ventricle pacing only), LR48 (biventricular pacing with a 48 ms delay left-right) . . . BIV0 (synchronous bi-ventricular pacing) . . . RL48 (bi-ventricular pacing with a 48 ms delay right-left) and R (right ventricular pacing only). For each of the nine configurations, the device measures the average value of the first PEAL peak, represented in 28 on FIG. 4. The average value of these nine values is then calculated, corresponding to the amplitude level illustrated in 30 on FIG. 4.

This parameter is considered as a good indication of the contractility state of the ventricles and also as a optional defect signal of the sensor (in case the amplitude value of the PEA is small or equal to zero on all or portions of the configurations). In this way, FIGS. 5a and 5b, homologous of FIG. 4, show the specificity of the parameter of that average PEA amplitude level for two different clinical examples. On those figures, the "S" letter indicates the configurations for which the characteristic profile has been considered as showing a satisfactory sigmoid factor. One can see that, for a given patient (the example illustrated in FIG. 5a), despite an important number of sigmoid profiles obtained, the average level of the PEA (30) is below the one from another patient for which the number of characteristic presenting a satisfactory sigmoid factor is lower (FIG. 5b).

Peak Endocardiac Acceleration Signal/Noise Ratio

An additional—and optional—parameter is obtained by quantifying the first PEAL peak signal/noise ratio, so as to get an indication of the signal quality compared to the mechanical and/or electrical noises.

As illustrated in FIG. 6, the PEAL value is measured based on the peak to peak amplitude of the first component of the endocardiac acceleration signal, detected during the iso-volumetric contraction phase of the ventricles, inside a first window (WEA1). The noise level (N1) is measured during the same cycle, in the interval separating the end of the WEA1 window and the beginning of the WEA2 window corresponding to the component of the second PEA2 peak. The noise can also be measured in N2, after the end of the WEA2 window.

The signal/noise ratio is given by:

$$SNR_{PEA1}(n) = \frac{PEA1(n)}{2 \cdot \sigma_{noise}(n)},$$

$\sigma_{noise}(n)$ being characteristic of the noise variability during the n cycle.

In the example of FIG. 6, the following signal/noise value is obtained: SNR=16.30 for a PEA1 peak=0.397 g.

Determination of the clinical status of the Patient

From the different parameters explicated above, the algorithm determines the clinical status of the patient using a Boolean table explicated by the flow-chart on FIG. 7. The analysis is performed on two successive levels A1 and A2. The first level—A1—is based on the results of the PEA/AVD characteristic analysis: achievement or not of an optimal AV Delay (algorithm convergence) and number of profiles showing among the various configurations a sigmoid factor.

The algorithm checks first (test 40) that at least one optimal AVD (OAVD) has been automatically obtained by the algorithm and then verifies the number of profiles having a sigmoid factor greater than the predetermined threshold (SF≥1, 2). The evaluation is satisfactory if, for the nine different configurations, at least three of the characteristics have such a sigmoid profile. It is "insufficient" otherwise (test 42, 42').

The second level of analysis—A2—is designed to evaluate the general level of contractility, from a PEA amplitude average value and (optionally) from the PEA signal/noise ratio. The average value of the PEA is considered as "satisfactory" when it is ≥0.25 g (tests 44, 44' and 44") and "insufficient" in the contrary (bad ventricular contractility or sensor default). The signal/noise ratio ("SNR") will be considered as "satisfactory" if SNR (PEA1)≥6, and "insufficient" on the contrary (which reflects a bad capacity or an insufficient reliability of the pacing configuration optimization algorithms).

The patient status is considered as "good" (result #50) for a patient presenting a complete optimization (optimal AV Delay found automatically, at least three curves with a sigmoid factor, and with PEA1 and signal/noise ratio satisfactory levels). The "average" status (result #52) will be attributed to a patient for whom the optimization is only partial, that is for whom only one of the two conditions for the A1 level analysis are satisfied. This "average" status is also attributed (result #54) to a patient that has a complete optimization (the two A1 level analysis criteria are satisfied) but with signals whose amplitude or whose PEA signal quality is too poor, reflecting a bad cardiac contractility level or signals whose reliability is not sufficient. The "bad" status (result #56) will be attributed to a patient for which none of the two conditions of the A1 analysis level is verified. Such a patient probably does not have an efficient response to the resynchronization therapy and has, therefore, a high risk that his pathology deteriorates.

Finally, if the average level of the PEA amplitude is very low, this situation corresponds to non exploitable data or, eventually, an issue such as a sensor failure (result #58).

Evolution Versus Time of the Clinical Status of the Patient

Once, the clinical status of the patient corresponding to his situation at a given moment is defined in the manner described above, it will be appreciated that one can study the evolution of this status versus time. In particular, it is interesting to consider the evolution between two successive executions of the pacing configuration optimization algorithm, for example at T=0 during implantation, and during the follow-up visits at T=3 months and/or T=6 months.

FIGS. 8 and 9 show, for two different clinical cases, the evolution of these different parameters. Those figures illustrate, in the upper part, the PEAL peak amplitude levels in the various pacing configurations (corresponding to the examples of FIGS. 5a and 5b), with—for each of them—an indication of the presence or not of a recognized sigmoid profile for the PEA/AVD characteristic: the "S" letter indicates that this criteria is verified, the "+" symbol indicates those of the pacing configurations which has been selected as the best one by the optimization algorithm and the symbol "~" indicates configurations considered as roughly equivalent to the best configurations selected by the algorithm.

The following lines indicate, at T=0, T=3 months and T=6 months, the clinical status determined according to the invention (status according to PEA) as well as its evolution: "stable", "deteriorated" or "improved". According to a preferred embodiment of the invention, the patient status is considered as:

"improved" if, between two pacing configuration optimization phases, the clinical status indication has changed from: "bad" to "average" or from "average" to "good";

"stable" if the indication has not changed and stayed at an "average" or a "good" level "deteriorated" (or "still bad") if the indication has changed from "average" to "bad", from "good" to "average" or has remained "bad".

It is eventually possible to attribute an "improved" situation if, despite a same clinical status, the analysis reveals an increase number of characteristics presenting a sigmoid curve and/or an increased number of configurations for which it is possible to automatically get an optimal AV Delay (convergence of the algorithm).

The resulting evolution from the endocardiac acceleration analysis is compared on FIGS. 8 and 9 to the evaluation from a physician clinical examination, which is not necessarily the same. Indeed, in the example of the FIG. 8, between T=0 and T=3 months, according to the data issued from the analysis made according to the invention only, the patient status remained "stable", whereas the physician diagnosis was a deterioration (false positive) following a patient hospitalization (noted as HOS), in fact not in correlation with his cardiac pathology. In the example illustrated in FIG. 9, however, the analysis made according to the invention, allowed to detect a deterioration at T=6 months, not diagnosed by the traditional clinical examination (false negative). In this way, the invention provides a prediction of a heart failure episode (noted HF) that could possibly occur after the test performed at T=6 month.

One skilled in the art will appreciate that the present invention can be practiced by other than the embodiments disclosed herein, which are presented for purposes of illustration and not of limitation.

We claim:

1. A medical device for characterizing cardiac status of a patient equipped with an active implant having a biventricular cardiac resynchronization therapy, comprising:

means for bi-ventricular pacing at selected ones of a plurality of sites;

means for collecting an endocardiac acceleration signal (EA);

means for testing a plurality of different pacing configurations by changing at least one of the selected sites, a pacing pulse sequence applied to the selected sites, and a time interval between the application of the pacing pulses to the selected sites, means for searching for an optimal pacing configuration using said testing;

means for each tested pacing configuration, delivering a plurality of parameters derived from one of the two endocardiac acceleration peaks (PEA1, PEA2) that appear respectively during the iso-volumetric ventricular contraction and during the iso-volumetric ventricular relaxation; and means for characterizing a patient cardiac status comprising:

a) means for analyzing said plurality of parameters and deriving a corresponding plurality of different respective specific indications, and b) means for combining said specific indications in a composite indication of the patient clinical status representative of the patient response to the cardiac resynchronization therapy;

c) means for comparing each of said specific indications to predetermined respective criteria, wherein said comparison means further comprises means for comparing first level specific indications derived from a PEA/AVD characteristic and including:

i) a first specific indication indicating whether at least one optimal AV Delay has been reached, and ii) a second specific indication representative of the sigmoid factor of said PEA/AVD characteristic;

d) a Boolean table that provides a corresponding value of the composite indication in response to said comparison.

2. The device of claim 1 further comprising sweeping means for varying an AV Delay (AVO) between an atrial sensed or paced event and a consecutive ventricular pacing event, wherein the characterizing means further comprises means for analyzing a PENAVD characteristic, said PENAVD characteristic giving successive endocardiac acceleration peaks (PEA) as a function of the AV Delay.

3. The device of claim 2, wherein said characterizing means further comprises means for determining an optimal AV Delay (OAVD) by analysis of said PENAVD characteristic for a plurality of different biventricular pacing configurations, and wherein said composite clinical status indication depends on whether a valid optimal AV Delay has been reached, among all said different biventricular pacing configurations.

4. The device of claim 3 wherein said characterizing means further comprises means for modeling said PEA/AVO characteristic in three segments having two plateaus on opposite sides of a central segment, with a negative slope (14), and wherein said composite clinical status indication is a function of the relative position of said three segments.

5. The device of claim 2 wherein said characterizing means further comprises means for determining a representative factor of a sigmoid character of said PENAVD characteristic for a plurality of different biventricular pacing configurations, and wherein said clinical status composite indication is a function of said sigmoid factor.

6. The device of claim 5 wherein said composite clinical status indication is also a function of the number of configurations, among all the said different biventricular pacing configurations, for which said respective sigmoid factor is above a predetermined threshold.

7. The device of claim 1 wherein said characterizing means further comprises means for calculating an amplitude average value of the detected endocardiac acceleration peaks for a plurality of different pacing configurations, wherein said clinical status composite indication is a function of said average value.

8. The device of claim 1 wherein said characterizing means further comprises means for quantifying the signal/noise ratio of the detected endocardiac acceleration peak, wherein said composite clinical status indication is a function of the result of said signal to noise quantification.

9. The device of claim 1 wherein said comparison means further
comprises means for comparing a second level specific indications including:
   a third specific indication derived from an average value of the endocardiac acceleration peaks, and
   a fourth specific indication derivate from a quantification of the endocardiac acceleration peak signal/noise ratio.

10. The device of claim 1 wherein the characterizing means further comprises:
   means for analyzing an evolution versus time of at least two successive values of said composite clinical status indication, and
   means for deriving from said analysis an indication of the patient evolution indicator and of the risk that a heart failure episode occurs.

11. A medical device for characterizing cardiac status of a patient equipped with an active implant having a biventricular cardiac resynchronization therapy, comprising:
   a sensor for collecting an endocardiac acceleration signal;
   a circuit for testing a plurality of different pacing configurations, and for each different pacing configuration, finding a plurality of parameters derived from at least one of the two endocardiac acceleration peaks; and
   wherein the circuit is configured to characterize the cardiac status of the patient by using the plurality of parameters to determine (a) whether an optimal AV delay was reached during a pacing configuration and (b) a sigmoid factor of a PEA/AVD characteristic associated with the pacing configuration, wherein the circuit uses a lookup table to find the cardiac status associated with the determinations.

12. A method for characterizing cardiac status of a patient equipped with an active implant having a biventricular cardiac resynchronization therapy feature, comprising:
   using a sensor to collect an endocardiac acceleration signal;
   at a circuit, using the collected endocardiac acceleration signal to test a plurality of different pacing configurations, and for each different pacing configuration, finding a plurality of parameters derived from at least one of the two endocardiac acceleration peaks; and
   characterizing the cardiac status of the patient by using the plurality of parameters to determine (a) whether an optimal AV delay was reached during a pacing configuration, and (b) a sigmoid factor of a PEA/AVD characteristic associated with the pacing configuration, wherein the circuit uses a lookup table to find the cardiac status associated with the determinations.

* * * * *